(12) United States Patent
Troxler et al.

(10) Patent No.: US 6,369,381 B1
(45) Date of Patent: Apr. 9, 2002

(54) APPARATUS AND METHOD FOR CALIBRATION OF NUCLEAR GAUGES

(75) Inventors: Robert Ernest Troxler, Raleigh; Wewage Linus Dep, Chapel Hill; William Finch Troxler, Sr., Raleigh, all of NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

(21) Appl. No.: 09/240,117

(22) Filed: Jan. 29, 1999

(51) Int. Cl.[7] .............................................. G12B 13/00
(52) U.S. Cl. .................................... 250/252.1; 378/207
(58) Field of Search ........................ 250/252.1; 378/207

(56) References Cited

U.S. PATENT DOCUMENTS

| | | |
|---|---|---|
| 2,781,453 A | 2/1957 | Belcher et al. |
| 3,334,230 A | 8/1967 | Shaffer |
| 3,544,793 A | 12/1970 | Bless et al. |
| 3,683,187 A | 8/1972 | Tompkins |
| 3,843,887 A | 10/1974 | Morrison |
| 3,860,816 A | 1/1975 | Wilson |
| 4,039,809 A * | 8/1977 | Bailey .................... 250/390.05 |
| 4,150,289 A | 4/1979 | Rosauer et al. |
| 4,152,600 A | 5/1979 | Berry |
| 4,155,009 A | 5/1979 | Lieber et al. |
| 4,347,440 A | 8/1982 | Haas |
| 4,406,947 A | 9/1983 | Burton et al. |
| 4,442,701 A | 4/1984 | Cowherd et al. |
| 4,465,929 A | 8/1984 | Edgar |
| 4,524,279 A | 6/1985 | Christianson et al. |
| 4,587,623 A | 5/1986 | Regimand et al. |
| 4,694,165 A | 9/1987 | Proctor et al. |
| 4,701,868 A | 10/1987 | Regimand |
| 4,791,656 A | 12/1988 | Pratt, Jr. et al. |
| 5,221,842 A | 6/1993 | Shepherd |
| 5,376,803 A | 12/1994 | McFee et al. |
| 5,479,021 A | 12/1995 | Morgan et al. |
| 5,552,606 A | 9/1996 | Jones et al. |
| 5,835,555 A | 11/1998 | Barry et al. |
| 5,923,726 A | 7/1999 | Regimand |
| 6,050,725 A | 4/2000 | Regimand |

FOREIGN PATENT DOCUMENTS

| | | |
|---|---|---|
| EP | 0 655 262 B1 | 5/1995 |
| GB | 2 236 851 A | 4/1991 |
| WO | WO 98/57269 | 12/1998 |

OTHER PUBLICATIONS

Meisner, et al., "A New Measurement–While–Drilling Gamma Ray Log Calibrator", Transactions of the SPWLA 26th Annual Logging Symposium, 1985, Abstract, Society of Professional Well Log Analysts, Inc., Houston, TX.

"Litho–Density Tool Calibration", Aug. 1985, pp. 515–520, Soc. of Petroleum Engineers Journal.

(List continued on next page.)

Primary Examiner—Seungsook Ham
Assistant Examiner—Shun Lee
(74) Attorney, Agent, or Firm—Alston & Bird LLP

(57) ABSTRACT

The present invention is directed to a method and apparatus for calibrating nuclear gauges and confirming gauge calibrations that provide the accuracy of multiple block calibration methods without requiring multiple standardized calibration blocks of known density. The apparatus includes a support for receiving a nuclear gauge of the type having a radiation source and a radiation detector and a variable radiation filter operatively associated with the support for providing variable attenuation of radiation emitted from the radiation source. The variable radiation filter includes a block having an eccentrically located cavity and positioned for rotation about the central axis of the cavity. The filter may further include a fixed mass for further attenuating radiation discharge by the radiation source such that the energy spectrum produced by the filter substantially matches the energy spectrum of a solid block of material, such as a standardized calibration block.

50 Claims, 4 Drawing Sheets

OTHER PUBLICATIONS

"Three Block Calibration System For Troxler Surface Moisture–Density Gauges", May 1987, pp. 1–18, Troxler Electronic Laboratories, Inc. Research Triangle Park, NC.

"Model 2376—Two–Probe Density Gauge", 1972, pp. 1–24, Troxler Electronics Laboratories, Inc. Research Triangle Park, NC.

* cited by examiner

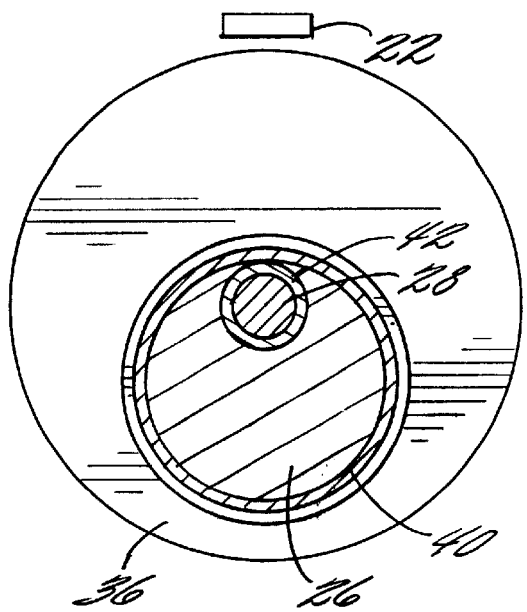
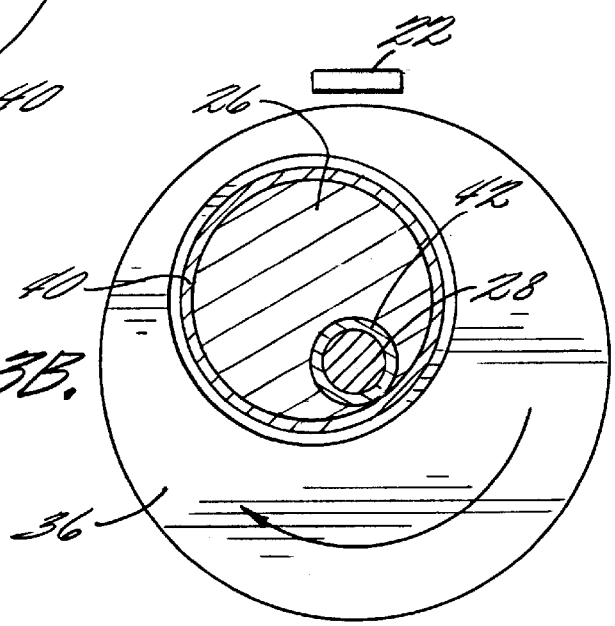
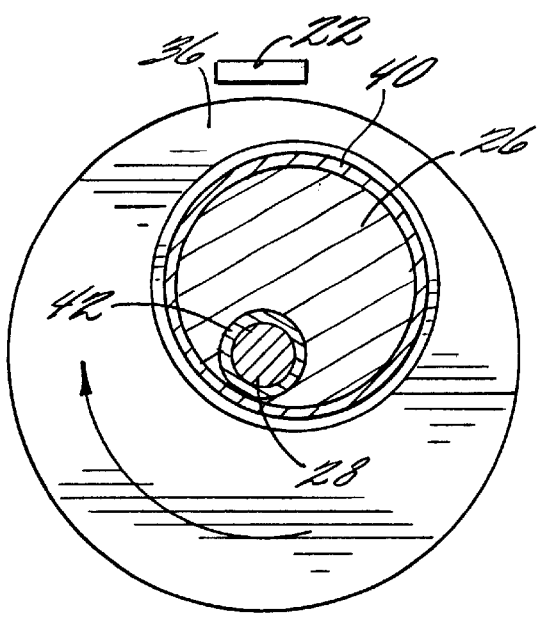

APPARATUS AND METHOD FOR CALIBRATION OF NUCLEAR GAUGES

FIELD OF THE INVENTION

The present invention relates to the calibration and calibration confirmation of nuclear gauges and, more particularly, relates to a method of calibrating such gauges without standardized calibration blocks.

BACKGROUND OF THE INVENTION

Nuclear radiation gauges are used to determine density and/or moisture content of soils, asphalt, and similar materials. Examples of such gauges are described in U.S. Pat. Nos. 2,781,453 and 3,544,793. In many instances, these gauges have become the industry standard because of their non-destructive testing capability and endurance. The American Society for Testing and Materials (ASTM) has established testing standards for using nuclear gauges to measure density and moisture content. The testing standards are designated D 2922-96 (density) and D 3017-88 (moisture) and are incorporated herein in their entirety.

Nuclear density gauges currently in use, for example, the Troxler Model 3400 and 4400 series gauges manufactured by the Assignee of the present invention, employ a nuclear radiation source, typically a mono-energetic source, that discharges gamma radiation into the test specimen and a radiation detector, typically a Geiger Mueller tube, that measures the scattered radiation. The gamma radiation interacts with matter in the test specimen, either by losing energy and changing direction (Compton interactions) or by terminating (photoelectric interactions). Consequently, the gamma radiation detected by the radiation detector has a continuous energy spectrum.

These gauges are designed to operate both in a "backscatter" mode and in a direct transmission mode. The radiation source is vertically moveable from a backscatter position where it resides within the gauge housing to a series of direct transmission positions where it is inserted into small holes or bores in the test specimen. The gamma radiation received by the radiation detector is related to the density of the test medium by an expression of the following form.

$$CR = A \exp(-BD) - C \qquad \text{Equation 1}$$

where:
- CR=count ratio (the accumulated photon count normalized to a reference standard photon count for purposes of eliminating long term effects of source decay and electronic drift),
- D=density of test specimen, and
- A, B, and C are constants.

The gauges are factory calibrated to arrive at values for constants A, B, and C for each gauge at each source depth position. The factory calibration procedure is a time-consuming iterative process, which may require several hours, or even days, to complete. In order to determine values for the three calibration parameters of the above equation, count measurements must be taken using at least three materials of different densities at each radiation source position. Typically, the three materials are solid blocks of aluminum, magnesium and a laminate of magnesium and aluminum. In some instances, as many as five calibration blocks of material have been employed in order to take into account the distinct mass attenuation coefficients of different soils. Thus, the standard factory calibration methods, often referred to as the three-block or five-block calibration methods, require a large number of individual counts in order to complete the calibration. For example, a gauge having a twelve-inch radiation source rod with seven different radiation source depth positions requires a minimum of twenty-one separate counts using the three-block calibration method. Each count is taken for a predetermined period of time, with longer periods of time producing greater precision. For example, for some gauge models, a typical count period for calibration is about four minutes for a direct transmission mode and about eight to twenty minutes for backscatter mode. Once all the counts are accumulated, values for the calibration parameters A, B, and C are calculated for each radiation source position.

The above-described calibration method is both time consuming and labor intensive because it requires numerous counts and movement of the gauge to positions overlying a plurality of blocks. The requirement that the gauge be moved from block-to-block also makes it difficult to fully automate the calibration process. Additionally, each standardized calibration block occupies a relatively large volume of space and weighs over 300 pounds, making them unwieldy and poorly suited for portability.

Further, in normal use, nuclear gauges undergo stress that can change the source-detector geometry of the gauge. Changes in geometry, as well as other factors, affect the gauge response such that, after a period of time, there is a need for recalibration of the gauge to arrive at new values for the constants A, B, and C. The standard practice in the industry has been to return the gauge to the factory, or to a regional calibration center, where the factory calibration process described above is repeated. Thus, the gauge user must go without the use of the gauge for a period of time while the gauge is recalibrated.

Efforts have been made to shorten the calibration process by using fewer standardized calibration blocks. For instance, in U.S. Pat. No. 4,587,623, incorporated by reference herein in its entirety, a calibration process using only two blocks is disclosed. This disclosed method relies on the assumption that the constant B, for a given radiation source position, does not change during the life of the gauge. However, the two-block method does sacrifice some accuracy since constant B may change slightly during the life of the gauge. Further, the two-block method still requires numerous counts and movement of the gauge between two heavy standard calibration blocks.

A calibration method using only one standard calibration block is disclosed in U.S. Pat. No. 4,791,656, which is incorporated by reference herein in its entirety. The one-block method involves a collection of counts from a single calibration block and the use of statistically derived relationships between the count rate actually obtained from the calibration block to the count rates historically obtained from at least two different calibration blocks of other known densities. By using such historically derived relationships, the expected calibration count rates for the other blocks can be estimated and used to calculate the equation parameters described above. Although the one-block method reduces the number of experimental counts that must be taken, it still requires the use of at least one heavy standardized calibration block. When using the one-block method, it is also generally advisable to confirm the calibration by testing the gauge on at least one other calibration block of substantially different density. A three block calibration process would still be required if the gauge failed to pass quality control/quality assurance tests. Further, by relying on the historically derived data, the one-block method assumes that, at a given source rod depth, there is a set of strong linear relationships that relate the magnesium, magnesium/aluminum and aluminum counts to one another. Some gauges, however, do not adhere to these relationships in a consistent manner. Such gauges would require a full three-block calibration process to ensure an adequate calibration. Finally, the one-block calibration procedure is only appropriate for calibrating gauges of identical construction as the gauges used to generate the historical data. So a one-block calibration process would be impossible for a new model or style of gauge because of the absence of historical data.

There remains a need for a new method of calibrating and confirming the calibration of nuclear gauges that is less time-consuming, less labor-intensive, and suitable for both initial factory calibrations and recalibrations by the gauge user at locations remote from the factory.

SUMMARY OF THE INVENTION

The present invention is directed to a method and apparatus for calibrating nuclear gauges that provides the accuracy of multiple block calibration methods without requiring multiple standardized calibration blocks of known density. Using the apparatus of the present invention, a nuclear gauge may be calibrated at each radiation source depth position without moving the gauge between multiple calibration blocks. Instead, the apparatus of the present invention utilizes a variable radiation filter capable of simulating the radiation attenuation of numerous materials of varying densities. In a preferred embodiment, the variable radiation filter simulates the density of multiple materials of known density, such as solid calibration blocks, and also attenuates the incident gamma radiation in such a way that the resulting energy spectra incident upon the gamma ray detectors substantially match the energy spectra of the materials of known density.

The apparatus of the present invention is useful for calibrating a nuclear gauge having a radiation source and a radiation detector. The apparatus comprises a support for receiving a nuclear gauge of the type having a radiation source and a radiation detector. Preferably, the support has a lateral surface adapted for receiving and supporting the underside of the nuclear gauge and an opening for receiving a vertically moveable source rod of a nuclear gauge therethrough. The support additionally includes a guide operatively positioned to guide a nuclear gauge into a position wherein said source rod of said gauge is overlying said cavity.

The apparatus further comprises a variable radiation filter operatively associated with the support and being located with respect to a nuclear gauge received on this support so as to attenuate radiation emitted from the radiation source. The radiation filter provides variable extents of radiation attenuation and is capable of simulating the radiation scattering of a plurality of materials having different densities. Preferably, the variable radiation filter comprises a mass of substantially uniform density mounted for movement relative to the support to present a variable extent of radiation attenuation to the radiation detector of the nuclear gauge. In one embodiment, the moveable mass comprises a block of predetermined shape, such as cylindrical, mounted for rotation relative to the support. The block has a cavity therein positioned beneath the opening of the support and adapted for receiving the source rod of the nuclear gauge. The cavity is eccentrically located within the block and the block is positioned for rotation about the central axis of the cavity, the axis of rotation being substantially perpendicular to the planar lateral support surface. In one embodiment, a motorized drive cooperating with the block rotates the block about the central axis of the cavity.

The variable radiation filter preferably includes a fixed mass operatively positioned adjacent to the radiation detector to further attenuate radiation emitted from the radiation source of the nuclear gauge. The fixed mass preferably comprises at least one plate constructed of material selected from the group consisting of aluminum, magnesium, lead, polyethylene, cadmium, tungsten, graphite and combinations thereof.

Preferably, the variable radiation filter produces energy spectra that substantially match the energy spectra of a plurality of materials having different densities. In one embodiment the variable radiation filter has a setting that simulates the density of magnesium, wherein the setting produces a ratio of total counts detected/counts with energy over 300 keV of at least about 4.0 at a radiation source depth of 2 inches measured by a 1-inch by 1-inch NaI scintillation detector. Most preferably, the ratio is at least about 4.5. Using the same magnesium setting at a radiation source depth of 8 inches, the setting produces a ratio of total counts detected/counts with energy over 300 keV of at least about 3.5, measured by a 1-inch by 1-inch NaI scintillation detector. Most preferably, the ratio is at least about 4.0.

In one embodiment, the variable radiation filter has a setting that simulates a known density and produces a ratio of total counts detected/counts with energy over 300 keV that is at least 70% of the same ratio produced by a solid block of material of the known density, as measured by a 1-inch by 1-inch NaI scintillation detector. Preferably, the ratio is about 80% of the ratio produced by a solid block of material of the known density. For example, the solid block of material could be a magnesium or aluminum calibration block.

The present invention also provides a method of calibrating a nuclear density gauge. The method includes providing a nuclear gauge having a radiation source and a radiation detector. The gauge is positioned on a calibration stand having a variable radiation filter such that radiation emanating from the source is attenuated by the filter. An accumulated count of scattered radiation is obtained with the nuclear gauge in position on the stand. The method may further include the step of adjusting the variable radiation filter to provide a different extent of radiation attenuation and obtaining a second accumulated count of scattered radiation with a nuclear gauge in the same position on the stand. The variable radiation may be adjusted to provide further different extents of radiation attenuation and further accumulated counts of scattered radiation may be obtained. For example, three or five different extents of radiation attenuation may be used to obtain a corresponding number of accumulated counts of scattered radiation.

Where the nuclear gauge is of the type having a radiation source located in a vertically moveable source rod, the source rod may be repositioned to a different source position while the gauge remains in position on the stand. In this manner, the gauge may be calibrated by obtaining accumulated counts of scattered radiation at each source depth position. Using the method of the present invention, the nuclear gauge may be calibrated at each source depth position by adjusting the variable radiation filter to provide one or more different extents of radiation attenuation and obtaining corresponding accumulated counts of scattered radiation without moving the gauge from the lateral support surface.

BRIEF DESCRIPTION OF THE DRAWINGS

Figure 2:
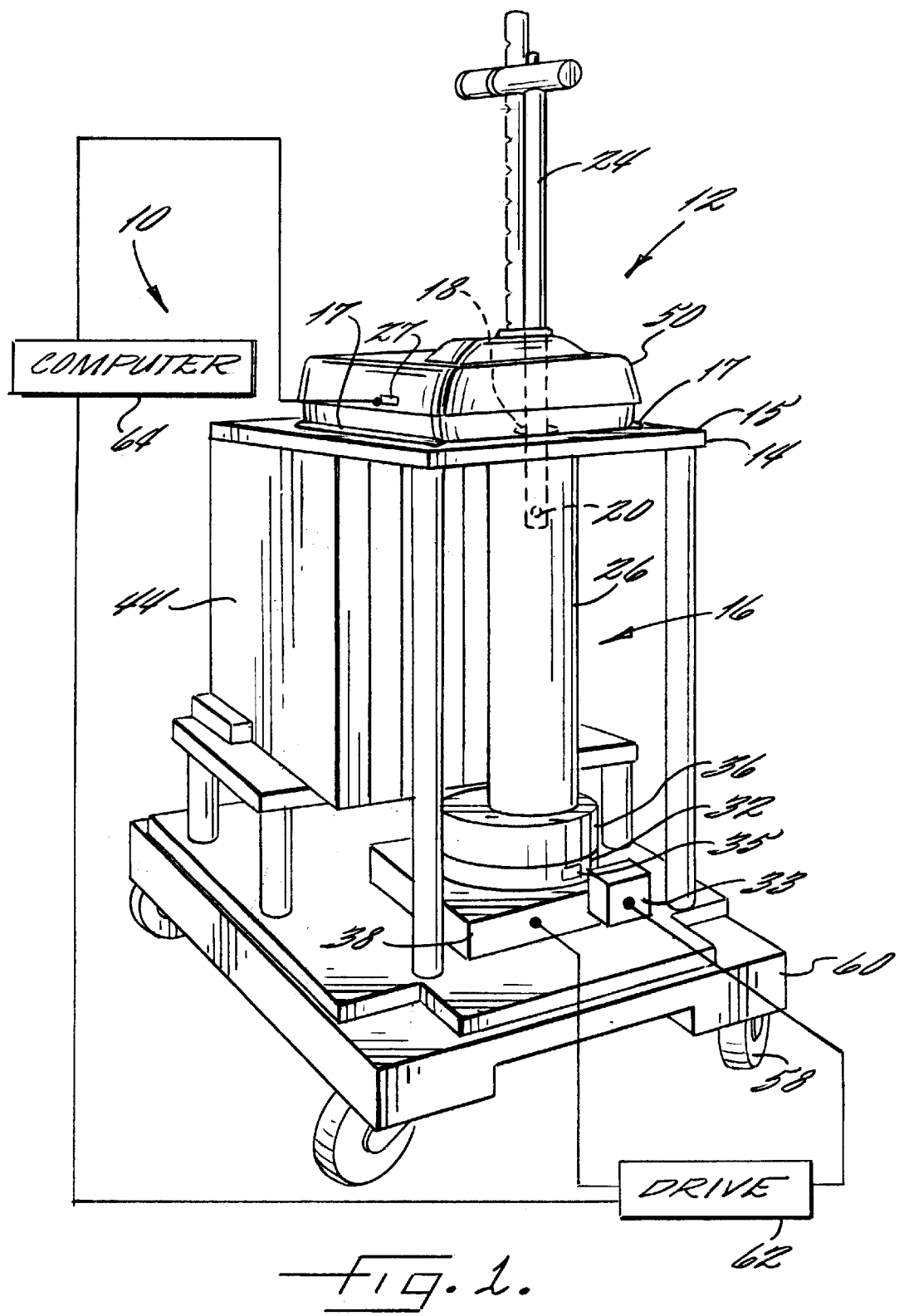
Figure 2:
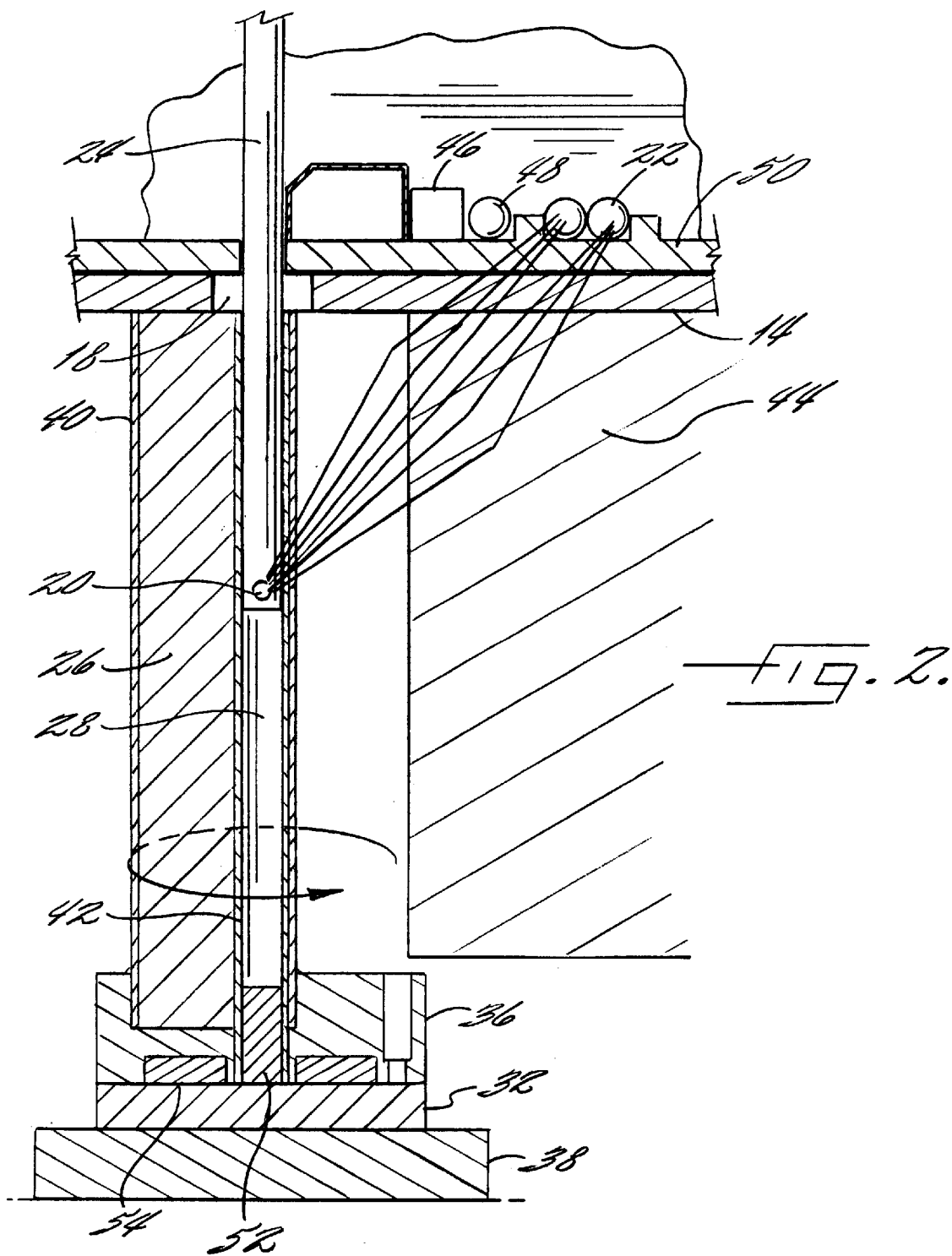
Figure 4:
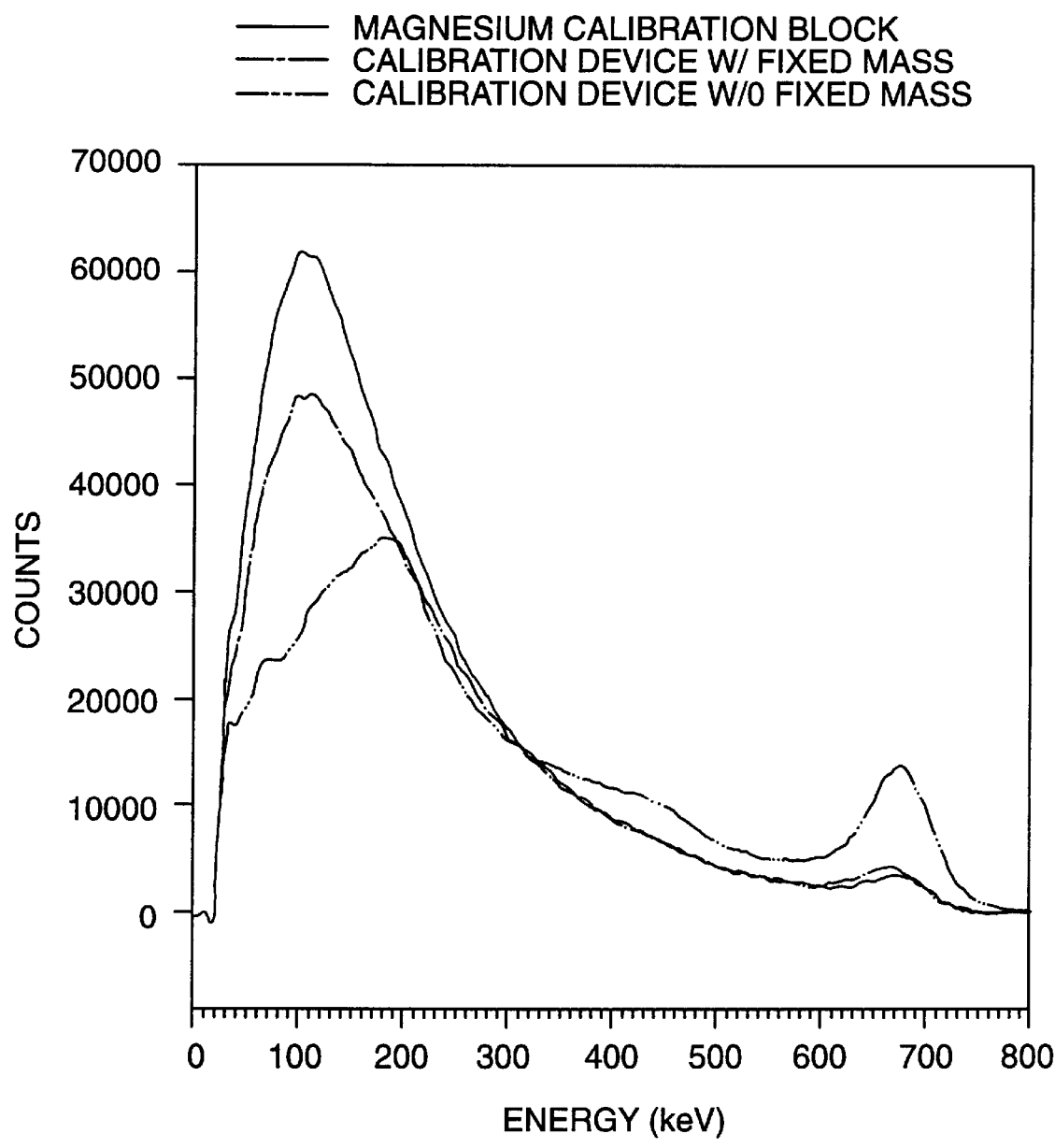

Having thus described the invention in general terms, reference will now be made to the accompanying drawings, which are not necessarily drawn to scale, and wherein:

FIG. 1 is a perspective view of an embodiment of the calibration apparatus of the present invention with a nuclear gauge positioned thereon;

FIG. 2 is a cross-sectional side view of an embodiment of the calibration apparatus of the present invention having a nuclear gauge positioned thereon;

FIGS. 3A–3C illustrate various positions of the variable radiation filter of the calibration apparatus; and FIG. 4 is a graphical comparison of the gamma ray energy spectra produced by a calibration block and two embodiments of the apparatus of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

FIG. 1 is a perspective view of the calibration apparatus 10 of the present invention having a nuclear gauge 12 placed thereon. As shown in FIG. 2, the nuclear gauge 12 comprises both a radiation source 20 and a radiation detector 22. The calibration apparatus 10 of the present invention may be used to calibrate nuclear gauges 12 in both backscatter mode and direct transmission modes. The particular type or configuration of the nuclear gauge 12 is not of critical importance to the present invention. As a result, the calibration apparatus 10 may be used with a variety of different nuclear gauges 12. In one commonly used configuration for a nuclear gauge, the radiation source 20 is mounted in a vertically moveable source rod 24, as shown in FIGS. 1 and 2. The nuclear gauge 12 may also include the capacity to measure moisture content. This type of gauge, as shown in FIG. 2, also contains a neutron source 46 and a neutron detector 48 within the nuclear gauge housing 50.

The apparatus 10 of the present invention includes a support 14 for receiving a nuclear gauge 12. The support 14 has a lateral surface 15, which receives and supports the underside of the nuclear gauge 12. The support 14 has an opening 18 that allows the vertically movable source rod 24 to descend freely. The support 14 includes a guide 17 in the form of abutments or rails, which is designed to guide the gauge 12 into proper placement on the support.

Below the opening 18 of the support 14 is a variable radiation filter 16. The variable radiation filter 16 is operatively associated with the support 14 and located with respect to the nuclear gauge 12 so as to attenuate radiation emitted from the radiation source 20. The variable radiation filter 16 of the present invention is capable of varying the extent of radiation attenuation, thereby simulating the radiation scattering of a plurality of materials having different densities. In a preferred embodiment, the variable radiation filter 16 comprises a mass of substantially uniform density mounted for movement relative to the support 14 in order to present a variable extent of radiation attenuation to the radiation detector 22 of the nuclear gauge 12. The filter 16 could be moved in various ways to provide the variable extent of radiation attenuation without departing from the present invention. As a non-limiting example, the filter 16 could be moved linearly in a longitudinal or transverse direction between the radiation source 20 and the radiation detector 22. In the embodiment shown, the moveable mass is a block 26 of predetermined shape mounted for rotation relative to the support 14. The predetermined shape of the block 26 is preferably cylindrical, but other shapes may be used without departing from the present invention. In one embodiment, the block 26 comprises a cylinder having a diameter of about two to about four inches.

By presenting a variable extent of radiation attenuation, the block 26 is capable of simulating the density of numerous materials, including traditional calibration blocks, such as magnesium or aluminum blocks. The block 26 simulates density by producing the same approximate count rate as produced by the material to be simulated at a given radiation source 20 depth. The block 26 also shields the user from exposure to excessive radiation.

Preferably, the block 26 has a cavity 28 positioned beneath the opening 18 in the support 14. The cavity 28 is eccentrically located within the block 26 and positioned to receive the vertically movable source rod 24. Preferably, the cavity 28 is deep enough to accommodate a standard length source rod 24. For instance, the cavity 28 is preferably deep enough to accommodate a source rod 24 capable of descending to a depth of 12 inches. Alternatively, the size of the block 26 can be reduced by allowing the block to move vertically with the source rod 24 such that the block only surrounds the portion of the rod containing the radiation source 20. The rotational axis of the block 26 is coincident with the rotational axis of the cavity 28. As shown in FIGS. 3A–3C, due to the eccentric location of the cavity 28 within the block 26, rotation of the block around the central axis of the cavity changes the amount of block material disposed between the radiation source 20 in the source rod 24 and the radiation detector 22 located within the housing 50 of the nuclear gauge 12. The change in the amount of material disposed between the radiation source 20 and the radiation detector 22 creates a corresponding change in extent of radiation attenuation provided by the variable radiation filter 16.

In one embodiment, the block 26 comprises an outer hollow aluminum cylinder 40 and an inner hollow aluminum cylinder 42. The inner hollow aluminum cylinder 42 defines the cavity 28 of the block 26. The space between the inner cylinder 42 and the outer cylinder 40 is filled with a radiation attenuating material, such as lead or tungsten. In the embodiment shown, the block 16 surrounds the radiation source 20, thereby providing shielding to prevent exposure of the user to excessive radiation.

Preferably, the block 26 is mounted on a base plate 36. The base plate 36 includes a ring-shaped lead shield 54 that surrounds the cavity 28 in the block 26. Further, a lead plug 52 is preferably located in the end of the cavity 28 located in the base plate 36. The lead ring 54 and lead plug 52 provide shielding to prevent excessive radiation discharging through the bottom of the calibration apparatus 10 when the source rod 24 is extended into the cavity 28.

In a preferred embodiment, the base plate 36 is mounted on a rotating platform 32. The rotating platform 32 allows rotational movement of the block 26/base plate 36 assembly. The rotating platform 32 is mounted on a platform support 38 and may be manually operated or include a motorized drive 62.

In one embodiment, a magnetic switch 33 is placed adjacent to the rotating platform 32. A magnet 35 is located on the outer surface of the rotating platform 32. The magnetic switch 33 is operatively connected to the motorized drive 62 such that rotation of the block 26/base plate 36 assembly may be stopped when the magnetic switch senses the proximity of the magnet 35. Thus, in the motorized embodiment of the present invention, the magnetic switch 33 allows orientation of the block 26 to an initial starting point. This enables the degree of rotation of the block 26 to be measured using a known reference point.

The variable radiation filter 16 preferably further includes a fixed mass 44. The fixed mass 44 is operatively positioned adjacent to the radiation detector 22 in order to further attenuate radiation emitted from the radiation source 20 of the nuclear gauge 12. Any given material produces a unique spectrum of energy when radiation is scattered therethrough. Even dissimilar materials having approximately the same density will produce different energy spectra when radiation is introduced into the material. The presence of the fixed mass 44 facilitates matching the energy spectrum of the variable radiation filter 16 to the energy spectrum produced by solid blocks of material, such as calibration blocks or field test materials such as asphalt. This allows more accurate simulation of the radiation scattering effect produced by traditional calibration blocks of known density, such as aluminum or magnesium blocks. The fixed mass 44 also shields the user from exposure to excessive radiation.

The block 26 is capable of simulating count rates associated with blocks of known density; however, in some embodiments, the block does not contain the proper material and volume to simulate the energy spectra of a solid block of known density. Each radiation detector 22, such as Geiger Mueller tube, has a different energy dependent efficiency function. For instance, a given detector 22 may exhibit strong detection sensitivity in the energy range of 200 keV to 300 keV and poor detection sensitivity in the energy range of 50 keV to 150 keV. The energy detection efficiency of the detector 22 impacts the accuracy of the gauge 12 calibration. If a gauge 12 is calibrated using an apparatus that simulates the count rates, but not the energy spectra, of traditional calibration blocks, the gauge may not receive an accurate calibration because of the difference between the detection efficiency of the "master gauge" used to prepare the density settings of the calibration apparatus 10 and the gauge to be calibrated. Using the fixed mass 44, the calibration apparatus 10 is capable of simulating both the count rate and the energy spectrum of a traditional calibration block, which enables the apparatus to reliably calibrate any gauge, regardless of energy detection efficiency.

The fixed mass 44 is much lighter than the solid blocks traditionally used to calibrate nuclear gauges 12 of the type contemplated by the present invention. Thus, the entire calibration apparatus 10 of the present invention is much lighter and more easily transportable. The calibration apparatus 10 may weigh as little as one third to one tenth of the weight of a standardized calibration block constructed of magnesium.

In a preferred embodiment, the fixed mass 44 comprises at least one plate constructed of a material selected from the group consisting of aluminum, magnesium, lead, polyethylene, graphite, cadmium, tungsten and combinations thereof, including composite or laminate structures. For example, the fixed mass 44 may include a plurality of planar magnesium and polyethylene plates affixed together to form a block-like mass. In one configuration, the fixed mass 44 comprises a combination of polyethylene and magnesium plates stacked side-by-side in the following order: polyethylene, magnesium, magnesium, magnesium, magnesium, and polyethylene. The polyethylene blocks are preferably about 3 inches thick with a width of about 9 inches and a height of about 11.5 inches. The magnesium blocks are preferably about one inch thick with a width of about 10 inches and a height of about 11.5 inches. In one embodiment, the fixed mass 44 further includes a cadmium plate or sheet (not shown) located above the magnesium and polyethylene plates and directly underneath the radiation support 14 in the approximate area of the radiation detector 22. However, many different configurations of the fixed mass 44 are possible. For instance, the number of plates, material of construction, shape of the plates and the position of each plate relative to the other plates may be adjusted as required to substantially match the desired energy spectrum.

To arrive at a workable configuration for the fixed mass 44, an energy spectrum analyzer, such as a scintillation detector-based multi-channel analyzer (MCA), may be employed to plot the unique energy spectrum of a given material. For example, a NaI scintillator coupled to a photomultiplier tube manufactured by Canberra may be utilized to measure the energy spectrum of a standardized calibration block. Once the spectrum is known, the fixed mass 44 may be adjusted to substantially match the energy spectrum of the calibration block.

Substantial matching of an energy spectrum is defined in terms of the ratio of total counts detected (C1)/counts with energy over 300 keV (C2) or the total-to-peak ratio defined as total counts detected (C1)/counts in the 662 keV peak (C3). These ratios assume the use of a 662 keV radiation source 20 (i.e. Cs-137). Further, these ratios are typically dependent on the geometry and type of detector used to measure the energy spectrum. The ratios used herein are based on the use of a 1-inch by 1-inch NaI scintillation detector.

At a radiation source 20 depth of 2 inches and at a density setting corresponding to a magnesium block, the ratio C1/C2 should be at least about 4.0, preferably at least about 4.5, and most preferably at least about 4.75. At a radiation source 20 depth of 4 inches and at a density setting corresponding to a magnesium block, the ratio C1/C2 should be at least about 3.5, preferably at least about 4.0, and most preferably at least about 4.4. At a radiation source 20 depth of 8 inches and at a density setting corresponding to a magnesium block, the ratio C1/C2 should be at least about 3.5, preferably at least about 4.0, and most preferably at least about 4.2.

The C1/C2 ratio calculated for a given source 20 depth and density setting of the apparatus 10 may also be compared to the C1/C2 ratio calculated using a calibration block having the same density. Preferably, for a given simulated density setting, the C1/C2 ratio calculated using the apparatus 10 (at any radiation source 20 depth) should be at least 70% of the C1/C2 ratio calculated using a calibration block having the same density. Most preferably, the C1/C2 ratio calculated using the apparatus 10 should be at least 80% of the C1/C2 ratio calculated using a calibration block of the same density. For example, if a setting of the block 26 simulates the density of magnesium, the C1/C2 ratio calculated at any radiation source 20 depth for that setting should be at least 70% of the same ratio calculated using a magnesium calibration block.

As shown in FIG. 1, in one embodiment, the calibration apparatus 10 of the present invention is supported on a lower platform 60. The calibration apparatus 10 of the present invention may further include wheels 58 for enhancing the transportability of the apparatus or handles (not shown) for lifting the apparatus.

In operation, a nuclear gauge 12 is first used to obtain a standard count as recommended by the gauge manufacturer.

The nuclear gauge 12 is then placed onto the calibration apparatus 10 with the source rod 24 exposed to the opening 18 in the support 14. The nuclear gauge 12 is precisely placed using the guide 17, which allow the source rod 24 and the cavity 28 within the block 26 to be precisely aligned. The source rod 24 is then placed at the desired calibration depth, either a backscatter mode where the source rod remains above the block 26 or a direct transmission mode where the source rod enters the cavity 28 of the block 26.

The block 26 is then rotated using the rotating platform 32 to a predetermined position that provides the radiation attenuation that corresponds to a known density. The rotation may be accomplished manually or by motorized drive 62. If adjusted manually, markings, such as precise detents, may be made on the apparatus, such as on the platform support 38, so that the block 26 may be precisely rotated to predetermined settings. If motorized, a computer 64 may be operatively coupled to the motorized drive 62 and used to input a specific density that the calibration apparatus 10 has been prepared to simulate. The computer 64 would then operate the motorized drive 62 and rotate the block 26 to a position or setting known to simulate the desired density.

One or more accumulated counts of scattered radiation may then be measured using the process suggested by the manufacturer of the nuclear gauge 12. After each count is measured, the block 26 is rotated to another predetermined setting corresponding to another known density. If a one-block calibration method is used, a single accumulated count of scattered radiation taken using a single predetermined setting of the block 26 is sufficient to calibrate the nuclear gauge 12 at that source depth position. Similarly, two accumulated counts of scattered radiation could be collected using two predetermined settings of block 26 and used in a two-block calibration method, in conjunction with the known value of constant B, to calibrate the nuclear gauge 12 at a given source depth position. Finally, three or more accumulated counts of scattered radiation may be measured and used to calculate the three constants found in Equation 1. Thus, the calibration apparatus 10 of the present invention may be used to perform a one-block, two-block, or any other multiple block calibration method. If a one-block calibration method is used, it is preferable to confirm the accuracy of the calibration by obtaining at least one additional accumulated count using at least one additional predetermined setting of block 26. For example, one of the confirmation processes described below may be used to confirm the accuracy of the calibration. Each count may be taken for a period of time recommended by the gauge manufacturer. Typically, for calibration, a count is taken over a four-minute period for direct transmission modes and between eight and twenty minutes for backscatter mode.

Preferably, the accumulated counts are input into a curve-fitting routine whereby the calibration constants of Equation 1 are calculated. This data could be loaded either manually or via an RS-232 interface into a computational device. The computational device could be embodied in a separate hand-held calculator, a computer integrated into the calibration apparatus 10, or the microprocessor of the nuclear gauge 12. The new constants may then be loaded into the gauge 12. For example, if a computer 64 is used, the computer may be used to input the constants into the gauge 12 via port 27.

Depending on which calibration method is being employed, the required number of accumulated counts of scattered radiation may be obtained at each additional radiation source depth. Thus, the entire procedure described above may be repeated for each depth setting of the radiation source 20. For example, the above procedure may be repeated in the backscatter mode, two-inch direct transmission mode, four-inch direct transmission mode, and the like. Due to the finite extent of the block 26, slight differences in the density measurement are perceived between different radiation source depths using the same block setting or orientation. These differences can be accounted for by assigning slightly different densities to each radiation source depth position for each block setting. This simplified approach requires preparation of only three block settings to enable the calibration apparatus 10 to perform a three-block calibration method and is particularly suitable for manual operation of the present invention where the block is adjusted to each setting by the user.

Alternatively, if it is desired that the calibration apparatus 10 simulate a specific density value at all radiation source depths, the density measurements may be equalized at a predetermined value by assigning a slightly different block orientation or position to each radiation source depth. For example, if the calibration apparatus 10 is designed to simulate the density values of a magnesium calibration block, an aluminum calibration block and a magnesium/aluminum laminate calibration block, a separate block orientation or position may be assigned to each radiation source depth for each desired density so that the calibration apparatus 10 simulates the same three density values at each radiation source depth. Since a greater number of block orientations are required, this method is particularly suited for automated operation of the present invention where a computer-controlled motorized drive 62 adjusts the block to each setting.

The calibration apparatus 10 may also be used to confirm or verify the calibration accuracy of a gauge 12 at periodic intervals in order to quickly ascertain whether the gauge is continuing to operate within predetermined quality control parameters. The calibration confirmation/verification method is similar to the calibration method described above. The calibration confirmation generally utilizes one, two or three points, depending on the density range that the gauge 12 encounters during use. If the gauge 12 is only used to measure a narrow range of densities, a one-point confirmation process is appropriate. A gauge application requiring a broader range of densities may require a two-point confirmation method. If the gauge 12 routinely measures densities over the entire dynamic range of the gauge calibration, a three-point confirmation is desirable.

In a one-point confirmation method, the gauge 12 is placed on the apparatus 10 of the present invention and the source rod 24 is lowered to the desired radiation source depth. The block 26 is rotated to a predetermined setting corresponding to a density that is within or near the narrow range of densities measured by the gauge 12. An accumulated count is taken for a predetermined count period. Typically, the count period is about one to about four minutes for calibration confirmation. The density measured by the gauge 12 is then compared to the accepted density value of the predetermined setting of the block 26 and the difference is evaluated using a quality control/quality assurance limit. For example, a typical quality control limit is about 1.0 lb/ft$^3$. If the difference between the measured and accepted density values is greater than the quality control limit, the gauge 12 fails the calibration confirmation and should be recalibrated. If the difference is within the quality control limit, the operation of the gauge 12 is acceptable and calibration is not required.

In the two-point confirmation method, two predetermined settings of the block 26 are used and two accumulated count measurements are taken. Preferably, the setting corresponding to the highest density value and the setting corresponding to the lowest density value are used. As with the one-point calibration, the difference between the accepted density value and the measured density is evaluated using a quality control limit.

The three-point confirmation method utilizes three predetermined settings of the block 26. The three settings are preferably spread out over the entire dynamic range of the original gauge calibration. As with the one and two-point confirmations, accumulated counts are taken at each setting and the corresponding densities are compared to the accepted density values for each setting. The difference between the measured density and the accepted density is evaluated using a quality control limit as described above.

In order to prepare the calibration apparatus 10, at least three settings corresponding to at least three known densities must be determined so that the calibration apparatus may be used in a one, two, or three-block calibration method. To determine the densities corresponding to the settings of the apparatus 10, a "master" gauge is used. The master gauge should be calibrated using the standardized calibration blocks used in the traditional three-block calibration method. Preferably, the master gauge is of the same type as the gauges that will be calibrated using the apparatus 10. Preferably, the master gauge is calibrated using longer count periods and stricter quality control/quality assurance limits. For example, during calibration of the master gauge, counting periods of approximately twenty minutes, rather than four minutes, may be utilized in direct transmission mode. Further, the measured density values are preferably evaluated using a strict quality control limit. For example, the quality control limit may require that the master gauge must fall within 0.2% of the accepted density value for each standardized calibration block.

In order to determine the settings for each calibration apparatus 10, the block 26 is rotated to a first position. The master gauge is placed on the calibration apparatus 10. An accumulated count of scattered radiation is measured using the procedure recommended by the gauge manufacturer. The block 26 may then be rotated to a second position in order to simulate a second extent of radiation attenuation. The master gauge is then used to take a second accumulated count of scattered radiation reading. The above steps may be repeated for as many settings as desired. Preferably, at least three settings are prepared for each calibration apparatus 10.

Since the calibration constants of the master gauge are known, the densities corresponding to the accumulated count readings may be calculated. In this manner, each rotational setting of the block 26 is associated with a known density. Note that it is preferable to choose the settings of the block 26 in such a manner as to provide a wide range of known densities. By using a wide range of densities, the accuracy of the calibration provided by the calibration apparatus 10 will be improved. For example, when using the three-block method, standardized blocks of magnesium, aluminum, and a block of laminated magnesium and aluminum are often used. The use of both magnesium and aluminum provides a good range of densities. Thus, while it is not necessary to exactly match the settings of the block 26 to the densities of known calibration blocks, such as magnesium calibration blocks, it is preferable to duplicate the approximate range provided by the use of aluminum and magnesium blocks.

Additionally, as discussed above, the accuracy of the calibration apparatus 10 is improved when a fixed mass 44 is used to substantially simulate the energy spectrum generated by radiation scattering through a block of solid material. Since traditional calibration blocks, such as magnesium and aluminum, are available and the energy spectrum associated with such blocks may be easily plotted using a spectrum analyzer, it is advisable to roughly match the densities simulated by the apparatus 10 to the densities of blocks having known energy spectrums. The fixed mass 44 may then be adjusted to substantially match the known energy spectra of materials having the same approximate density as the density simulated by the calibration apparatus 10. Thus, both the simulated count rates and energy spectrum of each predetermined setting will substantially match the count rates and energy spectrum of a known material commonly used for nuclear gauge calibration, resulting in better calibration accuracy and precision.

Since the master gauge is calibrated using blocks whose gravimetric densities are measured using instruments calibrated with NIST standards, the traceability of the densities associated with the settings of the block 26 are substantially equivalent to the traceability of densities assigned to commonly used standardized calibration blocks. Thus, there is no loss in calibration accuracy by using the calibration apparatus 10 of the present invention.

For nuclear gauges 12 that also measure moisture content, the calibration apparatus 10 may also be used to calibrate the moisture content measurement of the gauge. The relationship between moisture content and the thermal neutron count ratio is given by the following linear equation.

$$R = E + FM \qquad \text{Equation 2}$$

where,

R is the thermal neutron count ratio (ratio of actual count to standard count),

M is the moisture content of the test specimen, and

E and F are constants.

To obtain values for the two constants, two accumulated count readings are required. For calibration, the nuclear gauge 12 is first placed on the support 14. A first accumulated count reading is taken while the gauge 12 is in position on the support 14. A moisture plate (not shown) may then be placed between the gauge 12 and the support 14 to provide a different moisture content reading. The moisture plate may be constructed of any suitable material capable of simulating a certain amount of moisture content, such as polyethylene. A second accumulated count reading is taken while the gauge 12 is in position on the moisture plate. The moisture content values corresponding to the two accumulated counts may be determined by first obtaining accumulated counts using a 'master' gauge that has been previously calibrated using traditional moisture calibration blocks. For example, the master gauge may be calibrated using the calibration standards described in U.S. Pat. No. 4,152,600, which is hereby incorporated by reference in its entirety. The two accumulated counts collected using the gauge to be calibrated are then used to calculate new values for the constants E and F by solving Equation 2.

Alternatively, the calibration may be accomplished without the moisture plate by assuming an accumulated neutron count corresponding to a moisture content of 0. For any given gauge type or design, the accumulated neutron count corresponding to a moisture content of 0 will be relatively constant. A second accumulated count is taken while the gauge 12 is in position on the support 14. Using the assumed count and the accumulated count, new values for the two constants are calculated using Equation 2.

EXAMPLE 1

A master gauge, model M3440 manufactured by Troxler Electronic Laboratories of Research Triangle Park, N.C., was used to assign densities to three calibration apparatus orientations, designated O1, O2, and O3. Before using the master gauge, the calibration and stability of the gauge were verified. The assigned densities for the three orientations for a 4-inch source position were 109.9 (O1), 135.5 (O2), and 162.9 lbs/ft$^3$ (O3).

A standard count was taken for a test gauge, model M3430 manufactured by Troxler Electronic Laboratories. The standard count was 2725. The test gauge was placed on the calibration apparatus of the present invention with the source rod in 4-inch mode. Counts were accumulated for each apparatus orientation: O1, O2, and O3. Each count was taken over a four-minute period. The three accumulated counts acquired for the three orientations were 4398 (O1), 2620 (O2), and 1552 (O3). The same gauge was also calibrated using standardized calibration blocks. The calibration constants determined using the calibration apparatus are compared to the calibration constants determined using standardized calibration blocks in Table 1.

To determine the difference between the two calibrations, the values for A, B, and C calculated using the calibration blocks and the standard count were used to determine the ratio R (counts/standard counts) for a given density. The density equivalent for the calibration performed with the calibration apparatus of the present invention was then determined using the same R value and the values for A, B, and C calculated using the calibration apparatus. The density difference (dρ) between the two calibrations equals the absolute value of ($\rho_{cb}-\rho_{ca}$), wherein $\rho_{cb}$ is density determined using the constants calculated from calibration blocks and $\rho_{ca}$ is density determined using the constants calculated from the calibration apparatus. If the values of A, B, and C were identical for the two calibration methods, the density difference should be zero. The density difference between the two calibrations at 125 lbs/ft$^3$ was 0.10 lbs/f$^3$. The density difference for the range 110 to 165 lbs/ft$^3$ in 5 lbs/ft$^3$ steps was calculated in a similar way with an average dτ of 0.27 lbs/ft$^3$ over the entire range, indicating that the calibration apparatus of the present invention is capable of substantially matching the calibration accuracy provided by calibration blocks.

TABLE 1

| Method | A | B*1000 | C |
|---|---|---|---|
| Calibration Apparatus | 16.8349 | 1.3651 | −0.0920 |
| Calibration Blocks | 17.0467 | 1.3776 | −0.1084 |

EXAMPLE 2

The gamma-ray spectra received by the Geiger Mueller tubes of a nuclear density/moisture gauge was analyzed for various materials in both backscatter and direct transmission gamma-ray source positions. Spectra were acquired using a 1-inch by 1-inch NaI scintillation detector coupled to a photomultiplier tube. A Troxler model 3430 gauge without the neutron source, $^3$He detector, Geiger Mueller tubes, and gauge electronics was used. The active volume of the detector, i.e. the 1-inch by 1-inch NaI crystal, was placed at the middle of the area in the gauge base where the two Geiger Mueller tubes are normally placed. A 2-inch thick lead block was placed next to the NaI detector as a shield to prevent gamma rays hitting the crystal directly. It was discovered that each material-depth configuration has a unique gamma-ray spectrum.

FIG. 4 compares the spectra produced by a magnesium calibration block (with the radiation source 20 at a depth of four inches) with the spectra produced by two embodiments of the present invention. For each embodiment, a block 26 setting that simulates the density value of magnesium (~110 lbs/ft$^3$) at a radiation source depth of four inches was used. The solid line represents the energy spectrum of the magnesium calibration block. The double dash line represents the energy spectrum produced by the calibration apparatus 10 of the present invention without a fixed mass 44. The single dash line represents the energy spectrum produced by the calibration apparatus 10 of the present invention with a fixed mass 44. If the variable filter 16 of the calibration apparatus 10 cannot substantially match the energy spectrum of the material of known density that the apparatus is simulating, two gauges can read different densities (2 to 8 lbs/ft$^3$ apart) for the same block 26 setting. Experimentally, it has been determined that the connection between energy spectrum and differences in density readings between gauges results from the fact that two Geiger Mueller tubes can have different energy dependent gamma-ray detection efficiencies. As shown in FIG. 4, the apparatus 10 with the fixed mass 44 more closely approximates the energy spectrum of the magnesium block.

Tables 2–10 list the energy spectra data obtained using the 1-inch by 1-inch NaI scintillation detector coupled to a photomultiplier tube. The tables list data for 2-inch mode (Tables 2–4), 4-inch mode (Tables 5–7), and 8-inch mode (Tables 8–10). In each case, the count readings were taken using a magnesium calibration block and using a setting on the apparatus 10 that simulates the density of magnesium. For each depth mode, the tables show the relationships between peak height at low energy and peak height at 662 keV, total counts and counts over 300 keV, and total counts and counts in the 662 keV peak. As indicated by the data, the calibration apparatus 10 with the fixed mass 44 is capable of producing an energy spectrum that substantially matches the energy spectrum produced by the calibration block.

TABLE 2

(2-inch source depth)

| Device | Peak Height @ Low Energy (H1) | Peak Height at 662 KeV (H2) | Ratio (H1/H2) |
|---|---|---|---|
| Calibration Block | 62,244 @ 110 keV | 1,869 | 33.3 |
| Apparatus with fixed mass | 52,707 @ 120 keV | 2,568 | 20.5 |
| Apparatus without fixed mass | 44,421 @ 190 keV | 6,371 | 6.9 |

TABLE 3

(2-inch source depth)

| Device | Total Counts (C1) | Counts with Energy >300 keV (C2) | Ratio (C1/C2) |
|---|---|---|---|
| Calibration Block | 2,182,002 | 366,214 | 6.0 |
| Apparatus with fixed mass | 2,135,249 | 439,588 | 4.9 |
| Apparatus without fixed mass | 1,948,889 | 548,740 | 3.6 |

TABLE 4

(2-inch source depth)

| Device | Total Counts (C1) | Counts in the 662 keV peak (C3) | Ratio C1/C3 |
|---|---|---|---|
| Calibration Block | 2,182,002 | 7,488 | 291.7 |
| Apparatus with fixed mass | 2,135,249 | 11,873 | 180.9 |
| Apparatus without fixed mass | 1,948,889 | 52,174 | 37.4 |

TABLE 5

(4-inch source depth)

| Device | Peak Height @ Low Energy (H1) | Peak Height at 662 KeV (H2) | Ratio (H1/H2) |
|---|---|---|---|
| Calibration Block | 60,960 @ 110 keV | 3,719 | 16.4 |
| Apparatus with fixed mass | 47,900 @ 120 keV | 4,362 | 11.0 |
| Apparatus without fixed mass | 34,553 @ 190 keV | 13,709 | 2.5 |

TABLE 6

(4-inch source depth)

| Device | Total Counts (C1) | Counts with Energy >300 keV (C2) | Ratio (C1/C2) |
|---|---|---|---|
| Calibration Block | 2,278,909 | 454,481 | 5.0 |
| Apparatus with fixed mass | 1,991,407 | 455,658 | 4.4 |
| Apparatus without fixed mass | 1,880,130 | 701,194 | 2.7 |

TABLE 7

(4-inch source depth)

| Device | Total Counts (C1) | Counts in the 662 keV peak (C3) | Ratio (C1/C3) |
|---|---|---|---|
| Calibration Block | 2,278,909 | 21,427 | 106.5 |
| Apparatus with fixed mass | 1,991,407 | 27,461 | 72.5 |
| Apparatus without fixed mass | 1,880,130 | 124,125 | 15.1 |

TABLE 8

(8-inch source depth)

| Device | Peak Height @ Low Energy (H1) | Peak Height at 662 KeV (H2) | Ratio (H1/H2) |
|---|---|---|---|
| Calibration Block | 35,583 @ 110 keV | 2,025 | 17.6 |
| Apparatus with fixed mass | 29,234 @ 120 keV | 2,756 | 10.6 |
| Apparatus without fixed mass | 22,840 @ 190 keV | 9,248 | 2.5 |

TABLE 9

(8-inch source depth)

| Device | Total Counts (C1) | Counts with Energy >300 keV (C2) | Ratio (C1/C2) |
|---|---|---|---|
| Calibration Block | 1,294,769 | 266,185 | 4.9 |
| Apparatus with fixed mass | 1,186,617 | 282,955 | 4.2 |
| Apparatus without fixed mass | 1,211,977 | 453,537 | 2.7 |

TABLE 10

(8-inch source depth)

| Device | Total Counts (C1) | Counts in the 662 keV peak (C3) | Ratio (C1/C3) |
|---|---|---|---|
| Calibration Block | 1,294,769 | 13,448 | 96.6 |
| Apparatus with fixed mass | 1,186,617 | 15,179 | 78.1 |
| Apparatus without fixed mass | 1,211,977 | 91,028 | 13.3 |

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for calibrating a nuclear gauge having a radiation source and a radiation detector, comprising:
    a support for receiving a nuclear gauge of the type having a radiation source and a radiation detector; and
    a radiation filter capable of producing an energy spectrum incident upon the radiation detector that substantially matches the energy spectrum of at least one solid block of material, said filter comprising
        a variable radiation filter block operatively associated with said support and being so located with respect to a nuclear gauge received on said support as to attenuate radiation emitted from the radiation source, said radiation filter block having a variable extent of radiation attenuation capable of simulating the radiation scattering of a plurality of materials having different densities; and
        a fixed mass operatively positioned to further attenuate radiation emitted from the radiation source.

2. An apparatus according to claim 1, wherein said variable radiation filter block comprises a mass of substantially uniform density mounted for movement relative to said support to present a variable extent of radiation attenuation to the radiation detector of the nuclear gauge.

3. An apparatus according to claim 2, wherein said variable radiation filter block comprises a block of predetermined shape mounted for rotation relative to said support.

4. An apparatus according to claim 3, wherein said support has a lateral surface adapted for receiving and supporting the underside of a nuclear gauge, and wherein said variable radiation filter block is positioned beneath said support for rotation about an axis substantially perpendicular to said lateral support surface.

5. An apparatus according to claim 4, wherein the nuclear gauge is of the type having a radiation source located in a vertically moveable source rod, and said support has an opening therein for receiving the source rod therethrough, and said variable radiation filter block has a cavity therein positioned beneath said opening and adapted for receiving the source rod of the nuclear gauge, said cavity being eccentrically located within said block.

6. An apparatus according to claim 5, wherein said support additionally includes a guide operatively positioned to guide a nuclear gauge into a position wherein said source rod of said gauge is overlying said cavity.

7. An apparatus according to claim 5, wherein said block is positioned for rotation about the central axis of said cavity.

8. An apparatus according to claim 7, further comprising a motorized drive cooperating with said block for rotating it about said axis.

9. An apparatus according to claim 3, wherein said predetermined shape is cylindrical.

10. An apparatus according to claim 1, wherein said fixed mass comprises at least one plate constructed of material selected from the group consisting of aluminum, magnesium, lead, polyethylene, cadmium, tungsten, graphite and combinations thereof.

11. An apparatus according to claim 1, wherein said variable radiation filter block has a setting that simulates the density of magnesium, said setting producing a ratio of total counts detected/counts with energy over 300 keV of at least about b 4.0 at a radiation source depth of 2 inches measured by a 1-inch by 1-inch NaI scintillation detector.

12. An apparatus according to claim 11, wherein said ratio is at least about 4.5.

13. An apparatus according to claim 1, wherein said variable radiation filter block has a setting that simulates the density of magnesium, said setting producing a ratio of total counts detected/counts with energy over 300 keV of at least about 3.5 at a radiation source depth of 8 inches measured by a 1-inch by 1-inch NaI scintillation detector.

14. An apparatus according to claim 13, wherein said ratio is at least about 4.0.

15. An apparatus according to claim 1, wherein said variable radiation filter block has a setting that simulates a known density, said setting producing a ratio of total counts detected/counts with energy over 300 keV of at least 70% of the same ratio produced by a solid block of material of the known density, as measured by a 1-inch by 1-inch NaI scintillation detector.

16. An apparatus according to claim 15, wherein said ratio is about 80% of the ratio produced by a solid block of material of the known density.

17. An apparatus for calibrating a nuclear gauge having a radiation source and a radiation detector, comprising:
  a support having a lateral support surface for receiving and supporting the underside of a nuclear gauge of the type having a radiation source located in a vertically moveable source rod and a radiation detector, said support having an opening therein positioned for receiving the source rod therethrough;
  a radiation filter capable of producing an energy spectrum incident upon the radiation detector that substantially matches the energy spectrum of at least one solid block of material, said filter comprising
    a variable radiation filter block comprising a block of a radiation attenuating material of predetermined shape located beneath said support, said block having a vertical cavity therein positioned beneath said opening and adapted for receiving the source rod of the nuclear gauge, said cavity being eccentrically located within said predetermined shaped block; and
    a fixed mass operatively positioned beneath said support to further attenuate radiation emitted from the radiation source; and
  a mounting platform mounting said block for rotation about the central axis of said cavity so that the predetermined shape of the block presents a variable extent of radiation attenuation to the radiation detector of the nuclear gauge upon rotation of the block.

18. An apparatus according to claim 17, wherein said fixed mass comprises at least one plate constructed of material selected from the group consisting of aluminum, magnesium, lead, polyethylene, graphite, cadmium, tungsten and combinations thereof.

19. An apparatus according to claim 17, wherein said support additionally includes a guide positioned to guide a nuclear gauge into a position wherein said source rod of said gauge is overlying said cavity.

20. An apparatus according to claim 17, wherein said predetermined shape of said block is cylindrical, with the rotational axis of the cylinder coincident with the axis of said cavity.

21. An apparatus according to claim 17, wherein said variable radiation filter block has a setting that simulates the density of magnesium, said setting producing a ratio of total counts detected/counts with energy over 300 keV of at least about 4.0 at a radiation source depth of 2 inches measured by a 1-inch by 1-inch Na scintillation detector.

22. An apparatus according to claim 21, wherein said ratio is at least about 4.5.

23. An apparatus according to claim 17, wherein said variable radiation filter block has a setting that simulates the density of magnesium, said setting producing a ratio of total counts detected/counts with energy over 300 keV of at least about 3.5 at a radiation source depth of 8 inches measured by an 1-inch by 1-inch Nap scintillation detector.

24. An apparatus according to claim 23, wherein said ratio is at least about 4.0.

25. An apparatus according to claim 17, wherein said variable radiation filter block has a setting that simulates a known density, said setting producing a ratio of total counts detected/counts with energy over 300 keV of at least 70% of the same ratio produced by a solid block of material of the known density, as measured by a 1-inch by 1-inch NaI scintillation detector.

26. An apparatus according to claim 25, wherein said ratio is about 80% of the ratio produced by a solid block of material of the known density.

27. An apparatus for calibrating a nuclear gauge having a radiation source and a radiation detector, comprising:
  a support having a lateral support surface for receiving and supporting the underside of a nuclear gauge of the type having a radiation source located in a vertically moveable source rod and a radiation detector, said support having an opening therein positioned for receiving the source rod therethrough; and
  a radiation filter capable of producing an energy spectrum incident upon the radiation detector that substantially matches the energy spectrum of at least one solid block of material, said filter comprising
    a variable radiation filter block comprising a block of a radiation attenuating material of predetermined shape located beneath said support and mounted for movement relative to said support to present a variable extent of radiation attenuation to the radiation detector of the nuclear gauge, said block having a vertical cavity therein positioned beneath said opening and adapted for receiving the source rod of the nuclear gauge, said cavity being eccentrically located within said predetermined shaped block, and a fixed mass operatively positioned adjacent to the radiation detector to further attenuate radiation emitted from the radiation source of the nuclear gauge, wherein said variable radiation filter has a setting that simulates a known density, said setting producing a ratio of total counts detected/counts with energy over 300 keV of at least 70% of the same ratio produced by a solid block of material of the known density, as measured by a 1-inch by 1-inch NaI scintillation detector.

28. An apparatus according to claim 27, wherein said ratio is about 80% of the ratio produced by a solid block of material of the known density.

29. An apparatus according to claim 27, further comprising a mounting platform mounting said block for rotation about the central axis of said cavity so that the predetermined shape of the block presents a variable extent of radiation attenuation to the radiation detector of the nuclear gauge upon rotation of the block.

30. A method of calibrating a nuclear density gauge, comprising the steps of:

providing a nuclear gauge having a radiation source and a radiation detector;

positioning the gauge on a calibration apparatus comprising a radiation filter capable of producing an energy spectrum incident upon the radiation detector that substantially matches the energy spectrum of at least one solid block of material, the filter comprising a variable radiation filter block operatively positioned to attenuate radiation emitted from the radiation source, the filter block having a variable extent of radiation attenuation capable of simulating the radiation scattering of a plurality of materials having different densities, and a fixed mass operatively positioned to further attenuate radiation emitted from the radiation source; and obtaining an accumulated count of scattered radiation with the nuclear gauge in said position on the apparatus.

31. A method according to claim 30, further comprising the steps of adjusting the variable radiation filter block to provide a different extent of radiation attenuation; and obtaining a second accumulated count of scattered radiation with the nuclear gauge in said position on the apparatus.

32. A method according to claim 31, further comprising the steps of adjusting the variable radiation filter block to provide still another different extent of radiation attenuation; and obtaining a third accumulated account of scattered radiation with the nuclear gauge in said position on the apparatus.

33. A method according to claim 30, wherein the nuclear gauge is of the type having a radiation source located in a vertically moveable source rod and a radiation detector, and said method includes the further step of repositioning the source rod to a different source position while the gauge remains in said position on the calibration apparatus, and obtaining an additional accumulated count of scattered radiation with the nuclear gauge.

34. A method according to claim 30, further comprising the step of adjusting the variable radiation filter block to a setting that simulates the density of magnesium, said setting producing a ratio of total counts detected/counts with energy over 300 keV of at least about b 4.0 at a radiation source depth of 2 inches measured by a 1-inch by 1-inch NaI scintillation detector.

35. A method according to claim 34, wherein said ratio is at least about 4.5.

36. A method according to claim 30, further comprising the step of adjusting the variable radiation filter block to a setting that simulates the density of magnesium, said setting producing a ratio of total counts detected/counts with energy over 300 keV of at least about 3.5 at a radiation source depth of 8 inches measured by a 1-inch by 1-inch NaI scintillation detector.

37. A method according to claim 36, wherein said ratio is at least about 4.0.

38. A method according to claim 30, further comprising the step of adjusting the variable radiation filter block to a setting that simulates a known density, said setting producing a ratio of total counts detected/counts with energy over 300 keV of at least 70% of the same ratio produced by a solid block of material of the known density, as measured by a 1-inch by 1-inch NaI scintillation detector.

39. A method according to claim 38, wherein said ratio is about 80% of the ratio produced by a solid block of material of the known density.

40. A method of calibrating a nuclear density gauge, comprising the steps of:

providing a nuclear gauge having a radiation detector and a radiation source located in a vertically moveable source rod;

positioning the nuclear gauge on a calibration apparatus having a lateral support surface for receiving and supporting the underside of the nuclear gauge and a radiation filter capable of producing an energy spectrum incident upon the radiation detector that substantially marches the energy spectrum of at least one solid block of material, the filter comprising a variable radiation filter block operatively positioned to attenuate radiation emitted from the radiation source, the filter block having a variable extent of radiation attenuation capable of simulating the radiation scattering of a plurality of materials having different densities, and a fixed mass operatively positioned to further attenuate radiation emitted from the radiation source, the radiation source positioned at a predetermined source depth position; and obtaining an accumulated count of scattered radiation with the nuclear gauge in said position on the apparatus.

41. A method according to claim 40, further comprising the steps of adjusting the variable radiation filter block to provide a different extent of radiation attenuation; and obtaining a second accumulated count of scattered radiation with the nuclear gauge in said position on the apparatus.

42. A method according to claim 40, wherein the variable radiation filter block comprises a cylindrical block of a radiation attenuating material located beneath the support and mounted for rotation, and wherein the step of adjusting the variable radiation filter comprises rotating the cylindrical block to present a different extent of radiation attenuation to the radiation detector of the nuclear gauge.

43. A method according to claim 40, further comprising the steps of repositioning the radiation source to a different source depth position and obtaining an accumulated count of scattered radiation at the different source depth position.

44. A method according to claim 40, further comprising the steps of:

adjusting the variable radiation filter block to provide a second extent of radiation attenuation;

obtaining a second accumulated count of scattered radiation with the nuclear gauge in said position on the apparatus;

adjusting the variable radiation filter block to provide a third extent of radiation attenuation;

obtaining a third accumulated count of scattered radiation with the nuclear gauge in position on the apparatus; and calculating three constants A, B, and C in the following equation using the three accumulated counts and three known densities, $$CR = A\exp(-BD) - C,$$

wherein,

CR=the count ratio derived by comparing an accumulated count to a standard count, D=density, A, B and C=constants.

45. A method of calibrating a nuclear density gauge, comprising the steps of:

providing a nuclear gauge having a radiation detector and a radiation source located in a vertically moveable source rod;

positioning the nuclear gauge on a calibration apparatus having a lateral support surface for receiving and supporting the underside of the nuclear gauge and a radiation filter capable of producing an energy spectrum incident upon the radiation detector that substantially matches the energy spectrum of at least one solid block of material, the filter comprising a variable radiation filter block operatively positioned to attenuate radiation emitted from the radiation source, the filter block having a variable extent of radiation attenuation capable of simulating the radiation scattering of a plurality of materials having different densities, and a fixed mass operatively positioned to further attenuate radiation emitted from the radiation source, the radiation source positioned at a predetermined source depth position;

adjusting the variable radiation filter block to a predetermined setting, the setting corresponding to a first density;

emitting radiation from the radiation source;

detecting radiation using the radiation detector; and obtaining an accumulated count of scattered radiation with the nuclear gauge in said position on the apparatus, the ratio of total counts detected/counts with energy over 300 keV being at least 70% of the same ratio produced by a solid block having a first density, as measured by a 1-inch by 1-inch NaI scintillation detector.

46. A method according to claim 45, wherein said ratio is about 80% of the ratio produced by a solid block of material of the known density.

47. A method according to claim 45, wherein said solid block is a block selected from the group of magnesium, aluminum, polyethylene, graphite, cadmium, tungsten, lead and combinations, laminates and mixtures thereof.

48. A method of confirming a nuclear density gauge calibration, comprising the steps of:

providing a nuclear gauge having a radiation source and a radiation detector;

positioning the gauge on a calibration apparatus comprising a radiation filter capable of producing an energy spectrum incident upon the radiation detector that substantially matches the energy spectrum of at least one solid block of material, the filter comprising a variable radiation filter block operatively positioned to attenuate radiation emitted from the radiation source, the filter block having a variable extent of radiation attenuation capable of simulating the radiation scattering of a plurality of materials having different densities, and a fixed mass operatively positioned to further attenuate radiation emitted from the radiation source, the radiation source positioned at a predetermined source depth position;

adjusting the variable radiation filter block to a first predetermined setting corresponding to a first density;

obtaining an accumulated count of scattered radiation with the nuclear gauge in said position on the apparatus;

calculating the density corresponding to the accumulated count; and determining whether the difference between the calculated density and the first density exceeds a predetermined quality control limit.

49. A method according to claim 48, wherein the quality control limit is about 1.0 lbs/ft$^3$.

50. A method of calibrating a nuclear moisture gauge, comprising the steps of:

providing a nuclear gauge having a neutron detector and a neutron source;

positioning the nuclear gauge on a calibration apparatus comprising a lateral support surface for receiving and supporting the underside of the nuclear gauge and a radiation filter;

obtaining an accumulated neutron count with the nuclear gauge in said position on the apparatus;

assuming a neutron count corresponding to a moisture content of 0; and calculating two constants E and F in the following equation using the accumulated neutron count and the assumed neutron count, $$R = E + FM,$$

wherein,

R is the thermal neutron count ratio,

M is the moisture content, and

E and F are constants.

* * * * *

UNITED STATES PATENT AND TRADEMARK OFFICE
CERTIFICATE OF CORRECTION

PATENT NO. : 6,369,381 B1
DATED : April 9, 2002
INVENTOR(S) : Troxler et al.

It is certified that error appears in the above-identified patent and that said Letters Patent is hereby corrected as shown below:

Title page,
Item [56], References Cited, OTHER PUBLICATIONS, "Model 2376—Two Probe Design Gauge" reference, "Electronics" should read -- Electronic --.

Column 17,
Line 13, after "about" cancel "b".

Column 18,
Line 31, "Na" should read -- NaI --;
Line 39, "Nap" should read -- NaI --.

Column 20,
Line 1, after "about" cancel "b";
Line 34, "marches" should read -- matches --.

Signed and Sealed this

Twenty-fourth Day of December, 2002

JAMES E. ROGAN
*Director of the United States Patent and Trademark Office*